United States Patent
Ono et al.

(10) Patent No.: US 11,664,129 B2
(45) Date of Patent: May 30, 2023

(54) MINI-BATCH TOP-K-MEDOIDS FOR EXTRACTING SPECIFIC PATTERNS FROM CGM DATA

(71) Applicant: INTERNATIONAL BUSINESS MACHINES CORPORATION, Armonk, NY (US)

(72) Inventors: Masaki Ono, Tokyo (JP); Takayuki Katsuki, Tokyo (JP)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 730 days.

(21) Appl. No.: 16/539,523

(22) Filed: Aug. 13, 2019

(65) Prior Publication Data

US 2021/0050115 A1    Feb. 18, 2021

(51) Int. Cl.
*G16H 50/70* (2018.01)
*G06F 16/28* (2019.01)

(52) U.S. Cl.
CPC ........... *G16H 50/70* (2018.01); *G06F 16/285* (2019.01); *G06F 2216/03* (2013.01)

(58) Field of Classification Search
CPC .................. G16H 50/70; G06F 16/285; G06F 2216/03; G06F 16/906; G06K 9/6223
See application file for complete search history.

(56) References Cited

U.S. PATENT DOCUMENTS

| 9,165,052 B2 | 10/2015 | Rodinger et al. |
| 9,465,917 B2 | 10/2016 | Soni et al. |
| 2002/0188424 A1* | 12/2002 | Grinstein ............... G16B 25/10 702/183 |
| 2005/0114382 A1* | 5/2005 | Lakshminarayan .... G06F 18/23 707/999.102 |

(Continued)

FOREIGN PATENT DOCUMENTS

CN    104376057    2/2015

OTHER PUBLICATIONS

Chen, "Making Subsequence Time Series Clustering Meaningful", Fifth IEEE International Conference on Data Mining (ICDM'05), Nov. 2005, 8 pages.

(Continued)

*Primary Examiner* — Jason S Tiedeman
*Assistant Examiner* — Liza Tony Kanaan
(74) *Attorney, Agent, or Firm* — Tutunjian & Bitetto, P.C.; Randy Emilio Tejeda

(57) ABSTRACT

A method is provided for clustering data elements to extract specific patterns. The method specifies some data elements with a uniform distribution as a mini-batch and performs a single-pass cluster initialization by selecting a respective data element from the mini-batch as a respective initial cluster center to obtain cluster centers for clusters. The method assigns each data element in the mini-batch to a closest cluster by calculating a distance between each of the data elements in the mini-batch and each of the clusters. The method assigns k-minimum new centers by calculating an (Continued)

averaged distance to each data element in a same cluster. The method repeats the specifying step and the assigning steps responsive to a dissatisfaction of loop stop criteria which is based on distances between the centers and the K-minimum new centers. The method outputs a cluster id sequence responsive to a satisfaction of the loop stop criteria.

20 Claims, 7 Drawing Sheets

(56) References Cited

U.S. PATENT DOCUMENTS

| | | | | |
|---|---|---|---|---|
| 2005/0173021 A1* | 8/2005 | Muto | ............... | A61J 1/062 141/330 |
| 2006/0282236 A1* | 12/2006 | Wistmuller | ............... | G06N 3/02 703/2 |
| 2011/0191343 A1* | 8/2011 | Heaton | ............... | G16Z 99/00 707/E17.046 |
| 2015/0039619 A1* | 2/2015 | Zhang | ............... | G06F 16/285 707/738 |
| 2017/0251980 A1 | 9/2017 | Duke et al. | | |
| 2018/0296760 A1* | 10/2018 | Csenar | ............... | A61M 5/2033 |
| 2022/0066533 A1* | 3/2022 | Endoh | ............... | G06F 1/3275 |

OTHER PUBLICATIONS

Lu et al., "Constrained selective dynamic time warping of trajectories in three dimensional batch data", Chemometrics and Intelligent Laboratory Systems, Science Direct, Dec. 2016. 2 Pages.

Ide, "Theoretical basis for subsequence time-series clustering", The 20th Annual Conference of the Japanese Society for Artificial Intelligence, Jun. 2006, pp. 1-4.

Keogh et al., "Clustering of Time Series Subsequences is Meaningless: Implications for Previous and Future Research", Knowledge and Information Systems, Aug. 2005, 20 pages.

Wikipedia, K-medoids, aialable at: https://en.wikipedia.org/wiki/K-medoids. Last downloaded May 10, 2019, pp. 1-7.

Rodbard, "Continuous Glucose Monitoring: A Review of Successes, Challenges, and Opportunities", Diabetes Technology & Therapeutics, vol. 18, Supplement 2, Feb. 2016, pp. S2-3-S2-13.

Sculley, "Web-Scale K-Means Clustering", WWW 2010, Apr. 2010, 2 pages.

* cited by examiner

MINI-BATCH TOP-K-MEDOIDS FOR EXTRACTING SPECIFIC PATTERNS FROM CGM DATA

BACKGROUND

The present invention generally relates to medical intervention, and more particularly to a mini-batch top-k-medoid for extracting specific patterns from Continuous Glucose Monitoring (CGM) data. CGM is a type of temporal time-series data and has recently attracted attention regarding understanding the time series variation of glucose. However, there is a need for an approach to extract specific patterns from CGM data.

SUMMARY

According to an aspect of the present invention, a computer-implemented method is provided for clustering data elements to extract specific patterns from the data. The method includes specifying, by the hardware processor, some of the data elements with a uniform distribution as a mini-batch. The method further includes performing, by the hardware processor, a single-pass cluster initialization by selecting a respective one of the data elements from the mini-batch as a respective initial cluster center to obtain a plurality of cluster centers for a plurality of clusters. The method also includes assigning, by the hardware processor, each of the data elements in the mini-batch to a closest one of the plurality of clusters by calculating a distance between each of the data elements in the mini-batch and each of the plurality of clusters. The method additionally includes assigning, by the hardware processor, k-minimum new centers by calculating an averaged distance to each of the data elements in a same one of the plurality of clusters. The method further includes repeating, by the hardware processor, the specifying step and the assigning steps responsive to a dissatisfaction of loop stop criteria which is based on distances between the plurality of centers and the K-minimum new centers. The method also includes outputting, by the hardware processor, a cluster id sequence responsive to a satisfaction of the loop stop criteria.

According to another aspect of the present invention, a computer program product is provided for clustering data elements to extract specific patterns from the data. The computer program product includes a non-transitory computer readable storage medium having program instructions embodied therewith. The program instructions are executable by a computer to cause the computer to perform a method. The method includes specifying, by the hardware processor, some of the data elements with a uniform distribution as a mini-batch. The method further includes performing, by the hardware processor, a single-pass cluster initialization by selecting a respective one of the data elements from the mini-batch as a respective initial cluster center to obtain a plurality of cluster centers for a plurality of clusters. The method also includes assigning, by the hardware processor, each of the data elements in the mini-batch to a closest one of the plurality of clusters by calculating a distance between each of the data elements in the mini-batch and each of the plurality of clusters. The method additionally includes assigning, by the hardware processor, k-minimum new centers by calculating an averaged distance to each of the data elements in a same one of the plurality of clusters. The method further includes repeating, by the hardware processor, the specifying step and the assigning steps responsive to a dissatisfaction of loop stop criteria which is based on distances between the plurality of centers and the K-minimum new centers. The method also includes outputting, by the hardware processor, a cluster id sequence responsive to a satisfaction of the loop stop criteria.

According to yet another aspect of the present invention, a computer processing system is provided for clustering data elements to extract specific patterns from the data. The computer processing system includes a memory device including program code stored thereon. The computer processing system further includes a hardware processor, operatively coupled to the memory device, and configured to run the program code stored on the memory device to specify, some of the data elements with a uniform distribution as a mini-batch. The hardware processor further runs the program code to perform a single-pass cluster initialization by selecting a respective one of the data elements from the mini-batch as a respective initial cluster center to obtain a plurality of cluster centers for a plurality of clusters. The hardware processor also runs the program code to assign each of the data elements in the mini-batch to a closest one of the plurality of clusters by calculating a distance between each of the data elements in the mini-batch and each of the plurality of clusters. The hardware processor additionally runs the program code to assign k-minimum new centers by calculating an averaged distance to each of the data elements in a same one of the plurality of clusters. The hardware processor further runs the program code to repeat the specifying step and the assigning steps responsive to a dissatisfaction of loop stop criteria which is based on distances between the plurality of centers and the K-minimum new centers. The hardware processor also runs the program code to output a cluster id sequence responsive to a satisfaction of the loop stop criteria.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention are directed to mini-batch top-k medoids for extracting specific patterns from Continuous Glucose Monitoring (CGM) data.

In an embodiment, instead of defining distance between the cluster and a given element by a centroid of a cluster, some elements of the cluster are used for defining distance. This distance is then used to update cluster assignments.

Figure 1:
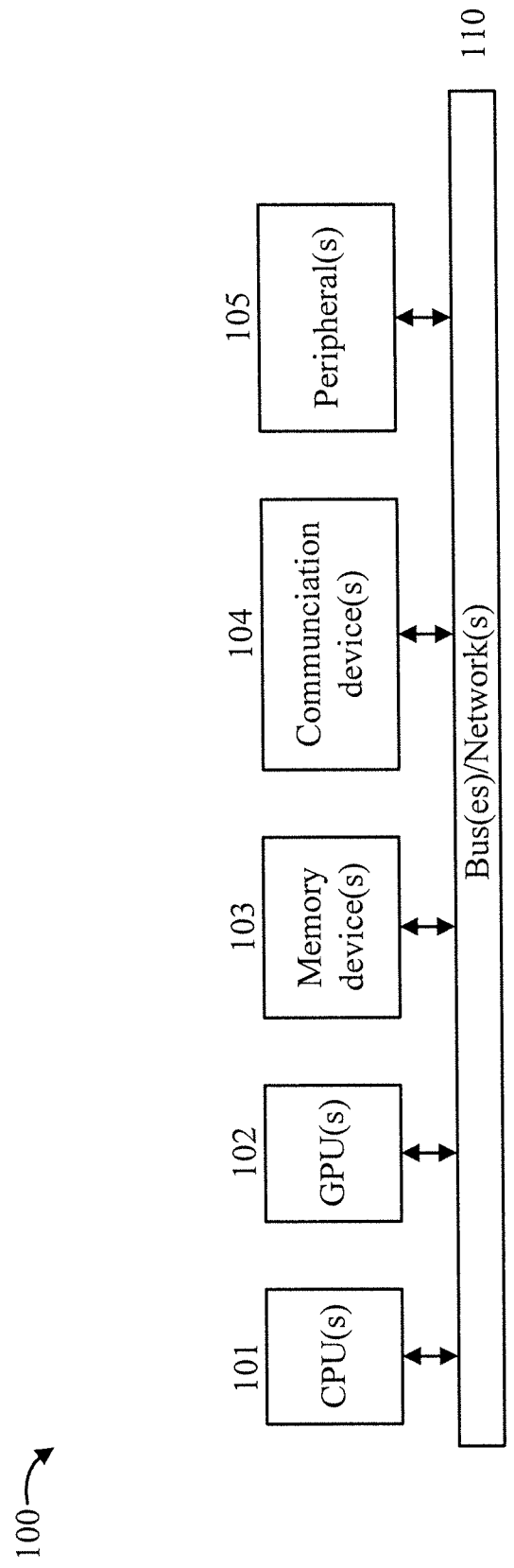
FIG. 1 is a block diagram showing an exemplary processing system, in accordance with an embodiment of the present invention.

FIG. 1 is a block diagram showing an exemplary processing system 100, in accordance with an embodiment of the present invention. The processing system 100 includes a set of processing units (e.g., CPUs) 101, a set of GPUs 102, a set of memory devices 103, a set of communication devices 104, and set of peripherals 105. The CPUs 101 can be single or multi-core CPUs. The GPUs 102 can be single or multi-core GPUs. The one or more memory devices 103 can include caches, RAMs, ROMs, and other memories (flash, optical, magnetic, etc.). The communication devices 104 can include wireless and/or wired communication devices (e.g., network (e.g., WIFI, etc.) adapters, etc.). The peripherals 105 can include a display device, a user input device, a printer, an imaging device, and so forth. Elements of processing system 100 are connected by one or more buses or networks (collectively denoted by the figure reference numeral 110).

In an embodiment, memory devices 103 can store specially programmed software modules to transform the computer processing system into a special purpose computer configured to implement various aspects of the present invention. In an embodiment, special purpose hardware (e.g., Application Specific Integrated Circuits, and so forth) can be used to implement various aspects of the present invention.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. Further, in another embodiment, a cloud configuration can be used (e.g., see FIGS. 6-7s). These and other variations of the processing system 100 are readily contemplated by one of ordinary skill in the art given the teachings of the present invention provided herein.

Moreover, it is to be appreciated that various figures as described below with respect to various elements and steps relating to the present invention that may be implemented, in whole or in part, by one or more of the elements of system 100.

Embodiments of the present invention are directed to the use of a top-k medoid for extracting specific patterns from CGM data. K-medoid is a clustering algorithm somewhat analogous to the k-means algorithm. Both K-medoids and k-means algorithms partition a dataset into groups and attempt to minimize a distance between points labeled to be in a cluster and a point designated as the center of that cluster. However, unlike the k-means algorithm, the k-medoid algorithm chooses data points as centers and can be used with arbitrary distances, while in the k-means algorithm, the center of a cluster is not necessary one of the input data points but is instead the average between points in the cluster.

K-medoid clusters the data set of n objects into k clusters, with the number k of clusters assumed to be known a priori. The quality of k can be evaluated using other methods as readily appreciated by one of ordinary skill in the art given the teachings of the present invention provided herein.

Figure 2:
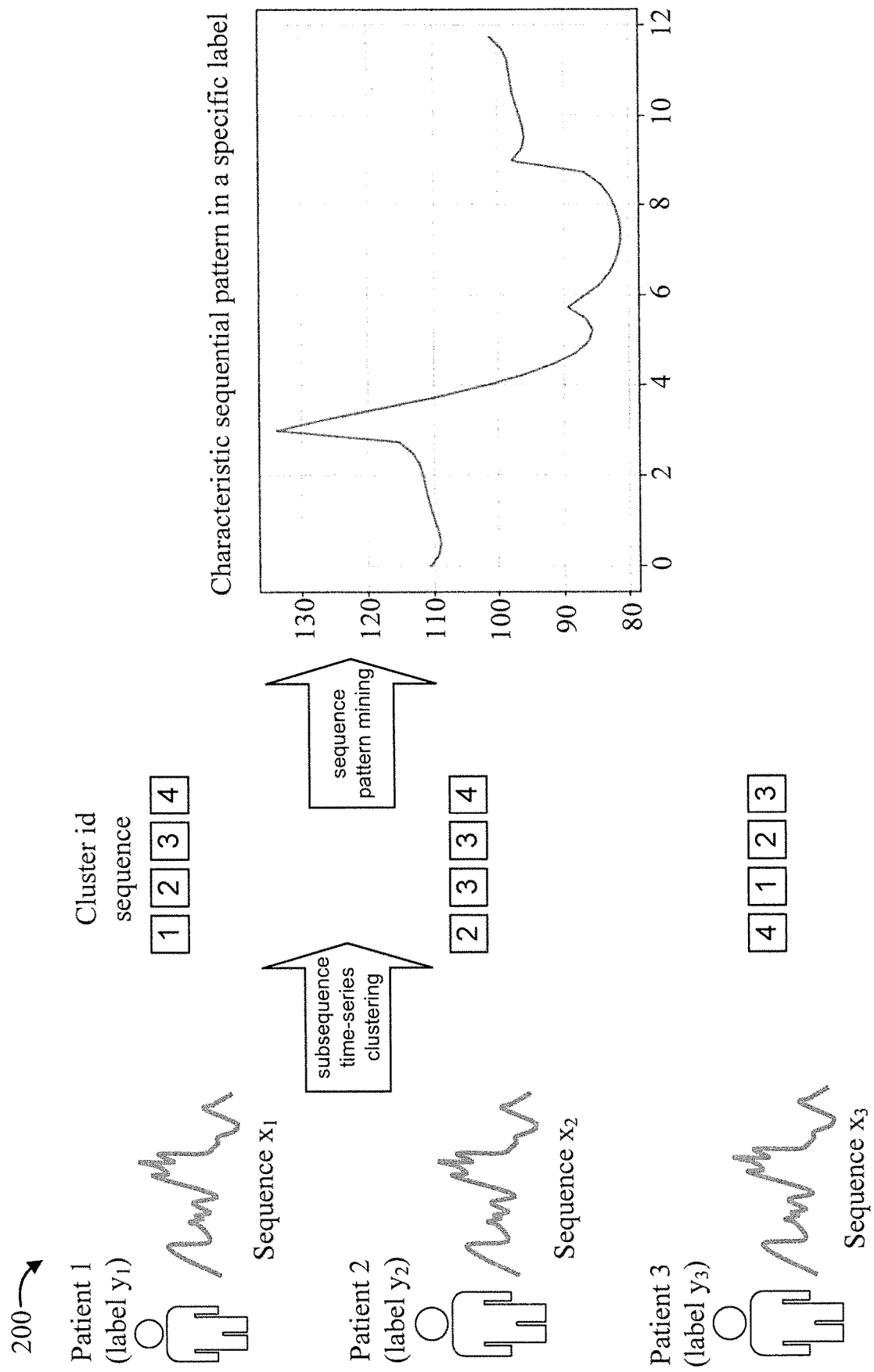
FIG. 2 is a diagram showing an exemplary application scenario, in accordance with an embodiment of the present invention.

FIG. 2 is a diagram showing an exemplary application scenario 200, in accordance with an embodiment of the present invention.

The scenario 200 involves patients patient 1 through patient n, labeled using labels $y_1$ through $y_n$, respectively, and producing sequences $x_1$ through $x_n$, respectively.

Subsequence time-series clustering 210 is performed on the sequences $x_1$ through $x_n$ in order to obtain cluster id sequences {1, 2, 3, 4}, {2, 3, 3, 4}, {4, 1, 2, 3}, respectively.

Sequence pattern mining 220 is performed on one or more of the cluster id sequences to obtain a characteristic sequential pattern in a specific label.

A description will now be given regarding various definitions, in accordance with one or more embodiments of the present invention.

$X = \{x_1, x_2, \ldots, x_n\}$ is a set of sub-sequences of given time-series data. All elements have the same dimension: $x_i \in \mathbb{R}^d$ $CLUSTER_i = \{G_1, G_2, \ldots, G_m\}$ is a set of clusters at step i $CENTER = \{C_1, C_2, \ldots, C_m\}$ is a set of centers for each cluster at step i $dist1(x_i, x_j) \to \mathbb{R}$ is a function which receives an element pair and calculates distance between them.

$dist2(X_i, x_j) \to \mathbb{R}$ is a function which receives centers of a cluster and an element and calculates distance between the cluster and the element.

$$dist2(X_i, x_j) = \frac{1}{|X_i|} \sum_{x \in X_i} dist1(x, x_j)$$

$dist3(C_i, C_j) \to \mathbb{R}$ is a function which receives a pair of centers and calculates distance between them.

$$dist3(C_i, C_j) = \frac{1}{|C_i| \times |C_j|} \sum_{x_i \in C_i} \sum_{x_j \in C_j} dist1(x_i, x_j)$$

Parameter:

m ∈ ℕ is the number of clusters;

k ∈ ℕ is the number of centers of a cluster;

b ∈ ℕ is the batch size; and delta ∈ ℝ is the threshold for distance between a pair of centers.

Figure 3:
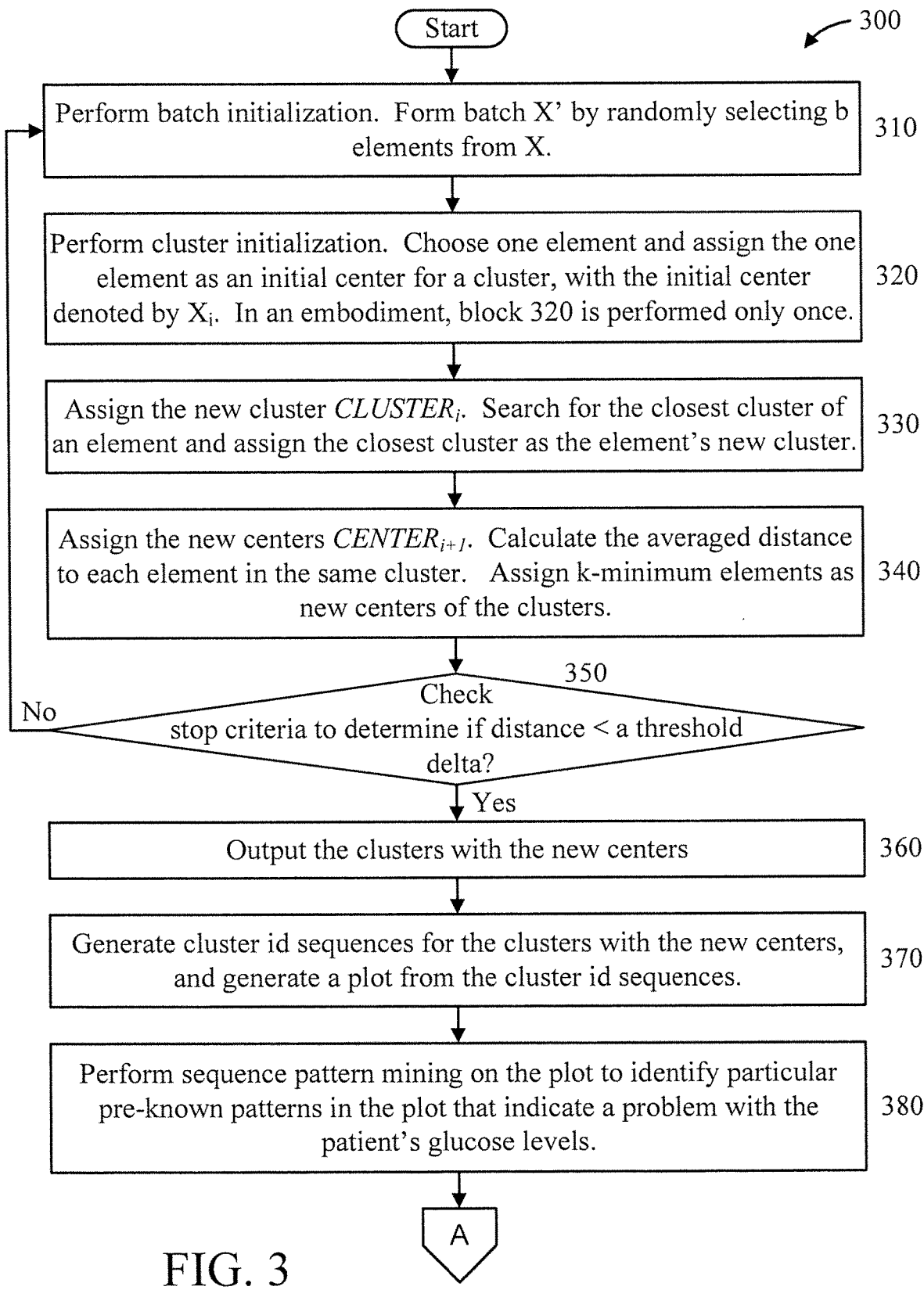
FIG. 3-4 are flow diagrams showing an exemplary method for extracting specific patterns from Continuous Glucose Monitoring (CGM) data.
Figure 4:
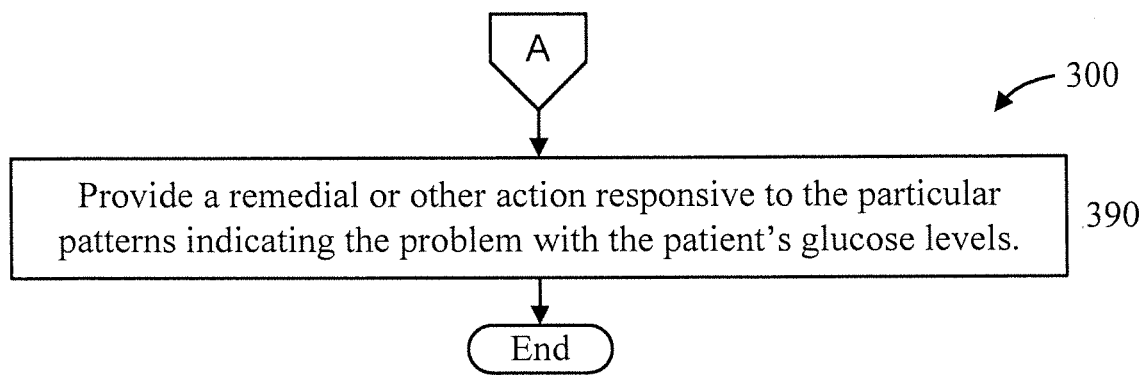

FIGS. 3-4 is a flow diagram showing an exemplary method 300 for extracting specific patterns from Continuous Glucose Monitoring (CGM) data.

At block 310, perform batch initialization. Form batch X' by randomly selecting b elements from X.

At block 320, perform cluster initialization. Choose one element and assign the one element as an initial center for a cluster, with the initial center denoted by $CENTER_1$. In an embodiment, block 320 is performed only once.

In an embodiment, the one element is chosen randomly. In an embodiment, the one element is chosen using a k-means++ initialization method (see, e.g., FIG. 5).

At block 330, assign the new cluster $CLUSTER_i$. Search for the closest cluster of an element and assign the closest cluster as the element's new cluster. In an embodiment, calculating the distance between a cluster and an element is performed using the dist2 function described herein. Of course, other distance functions can be used.

At block 340, assign the new centers $CENTER_{i+1}$. Calculate the averaged distance to each element in the same cluster. Assign k-minimum elements as new centers of the clusters. In an embodiment, calculating the distance between elements in a same cluster is performed using the dist1 function described herein. Of course, other distance functions can be used.

At block 350, check the stop criteria by calculating the distance between (initial) $CENTER_i$ (of block 310) and $CENTER_{i+1}$ (of block 340) to determine if the distance is less than a threshold delta. If so, then proceed to block 360. If not, return to block 310. In an embodiment, calculating the distance between a pair of centers is performed using the dist3 function described herein. Of course, other distance elements can be used.

At block 360, output the clusters with the new centers.

At block 370, generate cluster id sequences for the clusters with the new centers, and generate a plot or other representation (matrix, etc.) from the cluster id sequences. The cluster id sequences are generated by replacing i-th object with the cluster id that is assigned to i-th object.

At block 380, perform sequence pattern mining on the plot or other representation (matrix, etc.) to identify particular pre-known patterns in the plot that indicate a problem with the patient's glucose levels. Moreover, block 380 can involve detecting patterns having data points of the plot above a first threshold or below a second threshold to indicate an abnormal and/or otherwise unacceptable/non-optimal glucose level.

At block 390, provide a remedial or other action responsive to the particular patterns indicating the problem with the patient's glucose levels. For example, the remedial action can include alerting the user to a potentially problematic glucose level and/or providing or automatically dispensing a consumable item, an injection, and so forth to the user to alter the user's glucose levels to be within expected limits.

Figure 5:
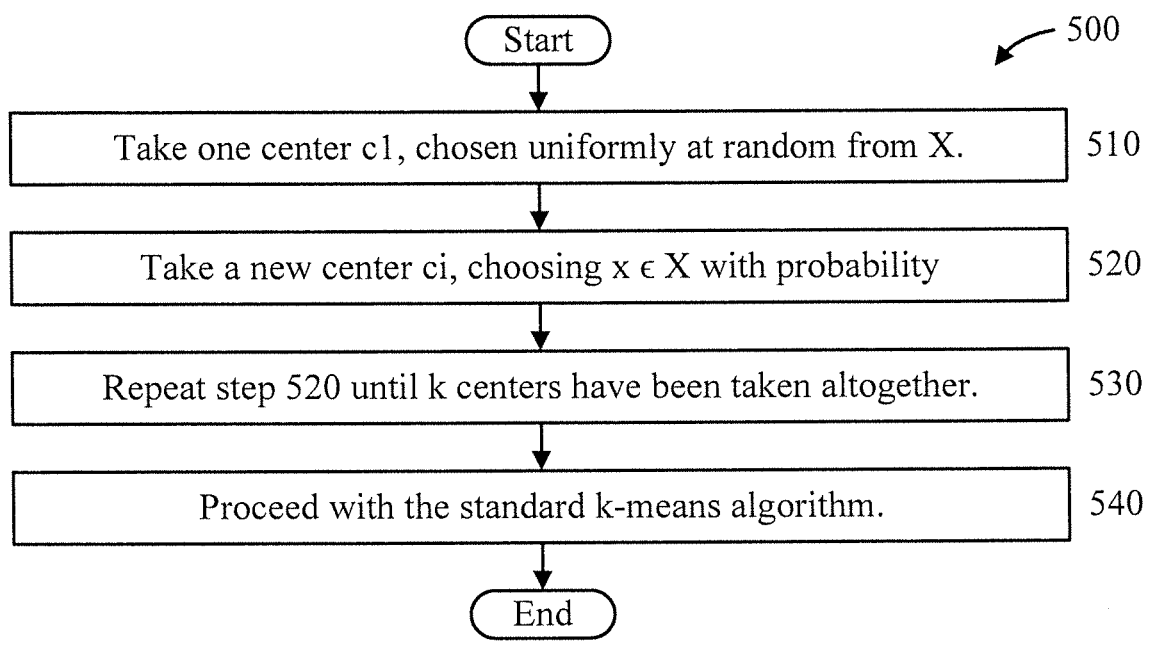
FIG. 5 is a flow diagram showing an exemplary method of choosing cluster centers, in accordance with an embodiment of the present invention.

FIG. 5 is a flow diagram showing an exemplary method 500 of choosing cluster centers, in accordance with an embodiment of the present invention. Method 500 is also interchangeably referred to as "k-means++ initialization method".

Let $D(x)$ denote the shortest distance from a data point to the closest center already chosen.

At block 510, take one center c1, chosen uniformly at random from X.

At block 520, take a new center ci, choosing $x \in X$ with probability $$\frac{D(x)^2}{\sum_{x \in X} D(x)^2}.$$

At block 530, repeat step 520 until k centers have been taken altogether.

At block 540, proceed with the standard k-means algorithm.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
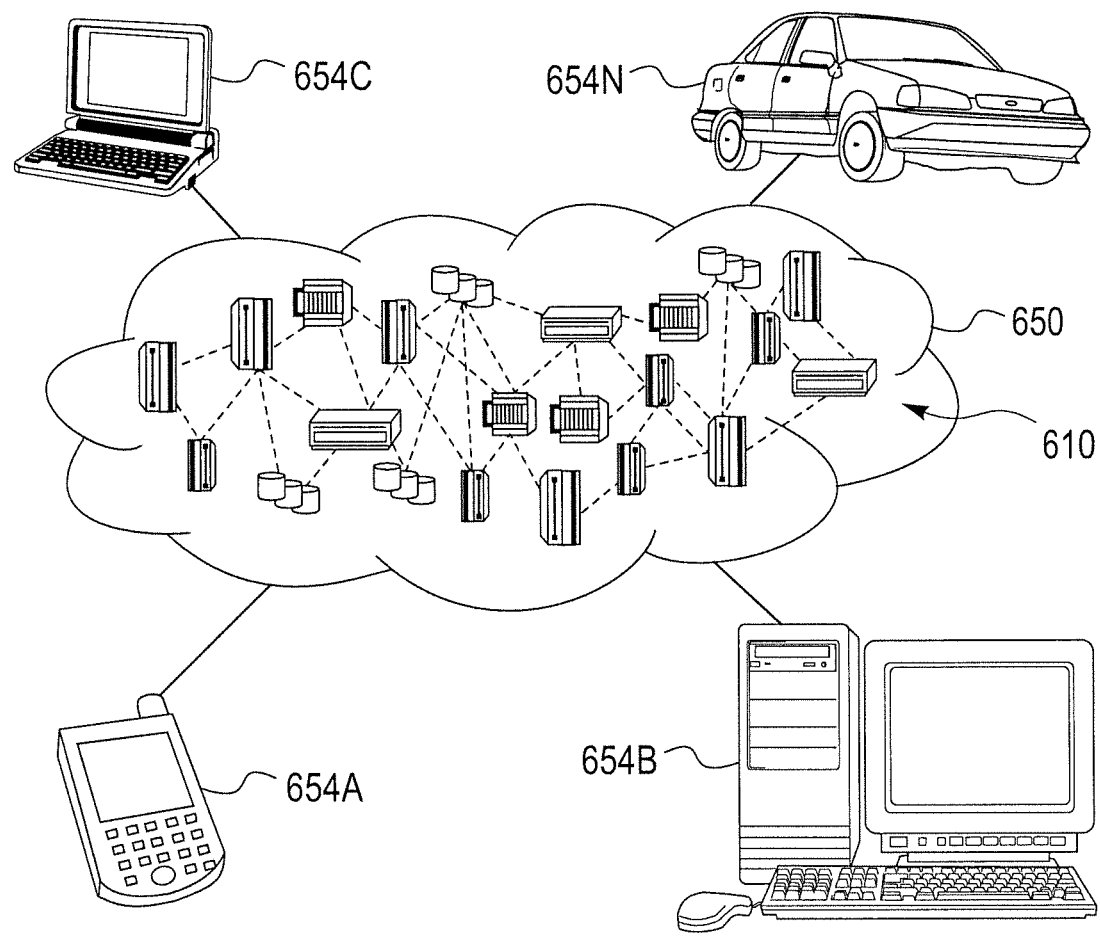
FIG. 6 is a block diagram showing an illustrative cloud computing environment having one or more cloud computing nodes with which local computing devices used by cloud consumers communicate, in accordance with an embodiment of the present invention.

Referring now to FIG. 6, illustrative cloud computing environment 650 is depicted. As shown, cloud computing environment 650 includes one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
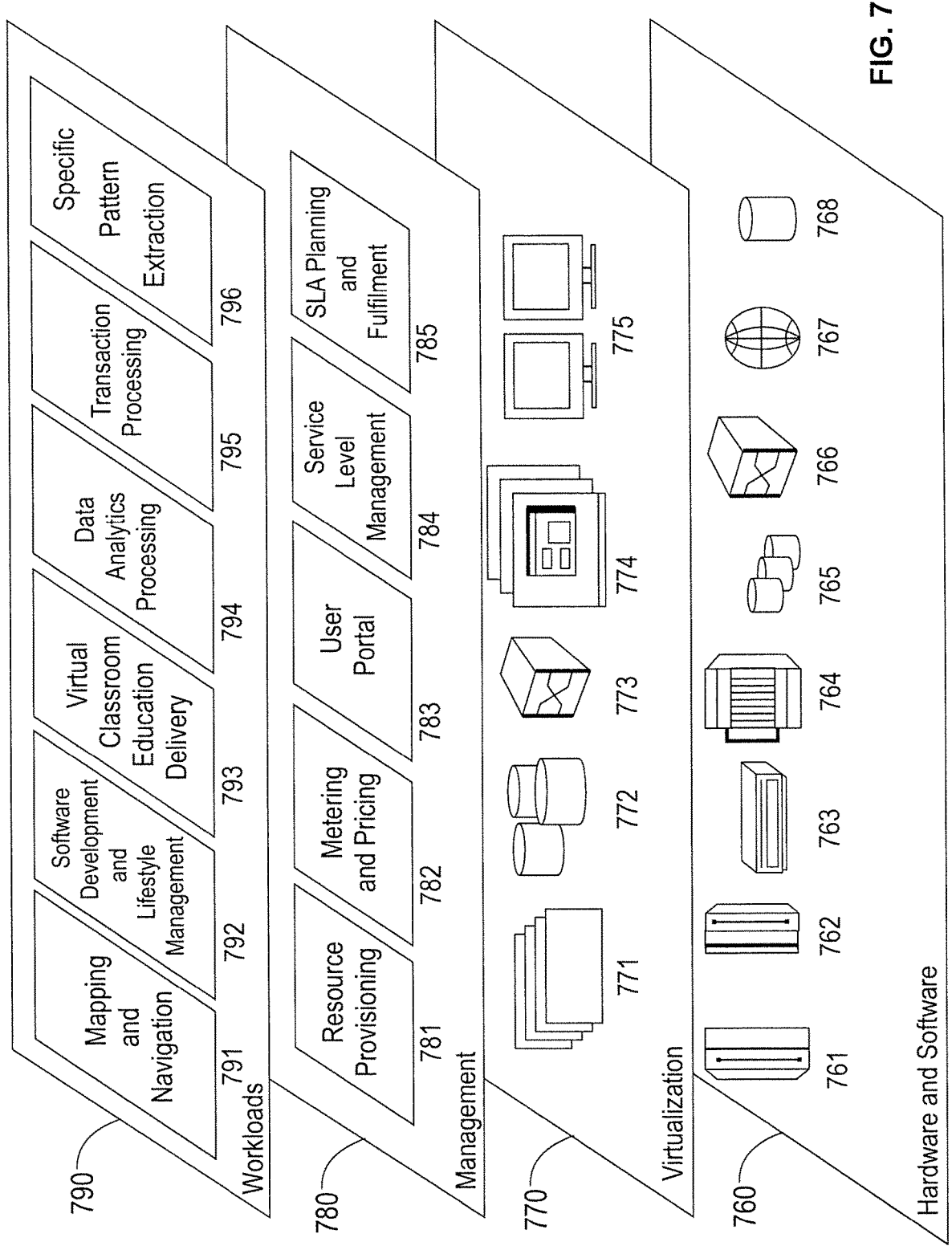
FIG. 7 is a block diagram showing a set of functional abstraction layers provided by a cloud computing environment, in accordance with an embodiment of the present invention.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and specific pattern extraction from CGM data 796.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for clustering data elements to extract specific patterns from the data, the method comprising;
   specifying, by a hardware processor, some of the data elements with a uniform distribution as a mini-batch;
   performing, by the hardware processor, a single-pass cluster initialization by selecting a respective one of the data elements from the mini-batch as a respective initial cluster center to obtain a plurality of cluster centers for a plurality of clusters;

assigning, by the hardware processor, each of the data elements in the mini-batch to a closest one of the plurality of clusters by calculating a distance between each of the data elements in the mini-batch and each of the plurality of clusters;

assigning, by the hardware processor, k-minimum new centers by calculating an averaged distance to each of the data elements in a same one of the plurality of clusters;

repeating, by the hardware processor, the specifying step and the assigning steps responsive to a dissatisfaction of loop stop criteria which is based on distances between the plurality of centers and the K-minimum new centers being greater than or equal to a threshold;

outputting, by the hardware processor, a cluster id sequence responsive to a satisfaction of the loop stop criteria based on the distances being less than the threshold; and automatically dispensing, by a dispenser under a control of the hardware processor, an injection into a user to alter glucose levels of the user within expected limits responsive to sequence pattern mining results, obtained from a plot of the plurality of clusters, indicating abnormal glucose levels.

2. The computer-implemented method of claim 1, wherein the single pass cluster initialization is limited to a single pass irrespective of a number of loop iterations.

3. The computer-implemented method of claim 1, wherein said performing step respectively selects one of the data elements randomly from the mini-batch as the respective initial cluster center to form the plurality of clusters.

4. The computer-implemented method of claim 1, wherein said specifying step randomly specifies some of the data elements with the uniform distribution as the mini-batch.

5. The computer-implemented method of claim 1, wherein said specifying step probabilistically specifies some of the data elements with the uniform distribution as the mini-batch.

6. The computer-implemented method of claim 1, wherein the data elements are comprised in time-series data and each of the data elements have a same dimension.

7. The computer-implemented method of claim 6, wherein the time series data comprises continuous glucose monitoring data, and the method further comprises:
deriving a cluster id sequence for a given patient from any of the plurality of clusters corresponding the given patient;
performing sequence pattern mining on the cluster id sequence to identify patterns pre-designated as problematic for the given patient.

8. The computer-implemented method of claim 1, wherein the sequence pattern mining is performed on a graph derived from the cluster id sequence.

9. The computer-implemented method of claim 1, further comprising commencing a loop prior to said specifying step, and ending the loop at the outputting step responsive to the satisfaction of the loop stop criteria.

10. The computer-implemented method of claim 1, wherein the distance is calculated using a non-Euclidean distance calculation function.

11. A computer program product for clustering data elements to extract specific patterns from the data, the computer program product comprising a non-transitory computer readable storage medium having program instructions embodied therewith, the program instructions executable by a computer to cause the computer to perform a method comprising:

specifying, by a hardware processor, some of the data elements with a uniform distribution as a mini-batch;

performing, by the hardware processor, a single-pass cluster initialization by selecting a respective one of the data elements from the mini-batch as a respective initial cluster center to obtain a plurality of cluster centers for a plurality of clusters;

assigning, by the hardware processor, each of the data elements in the mini-batch to a closest one of the plurality of clusters by calculating a distance between each of the data elements in the mini-batch and each of the plurality of clusters;

assigning, by the hardware processor, k-minimum new centers by calculating an averaged distance to each of the data elements in a same one of the plurality of clusters;

repeating, by the hardware processor, the specifying step and the assigning steps responsive to a dissatisfaction of loop stop criteria which is based on distances between the plurality of centers and the K-minimum new centers being greater than or equal to a threshold;

outputting, by the hardware processor, a cluster id sequence responsive to a satisfaction of the loop stop criteria based on the distances being less than the threshold; and automatically dispensing, by a dispenser under a control of the hardware processor, an injection into a user to alter glucose levels of the user within expected limits responsive to sequence pattern mining results, obtained from a plot of the plurality of clusters, indicating abnormal glucose levels.

12. The computer program product of claim 11, wherein the single pass cluster initialization is limited to a single pass irrespective of a number of loop iterations.

13. The computer program product of claim 11, wherein said performing step respectively selects one of the data elements randomly from the mini-batch as the respective initial cluster center to form the plurality of clusters.

14. The computer program product of claim 11, wherein said specifying step randomly specifies some of the data elements with the uniform distribution as the mini-batch.

15. The computer program product of claim 11, wherein said specifying step probabilistically specifies some of the data elements with the uniform distribution as the mini-batch.

16. The computer program product of claim 11, wherein the data elements are comprised in time-series data and each of the data elements have a same dimension.

17. The computer program product of claim 16, wherein the time series data comprises continuous glucose monitoring data, and the method further comprises:
deriving a cluster id sequence for a given patient from any of the plurality of clusters corresponding the given patient;
performing sequence pattern mining on the cluster id sequence to identify patterns pre-designated as problematic for the given patient.

18. The computer program product of claim 11, further comprising commencing a loop prior to said specifying step, and ending the loop at the outputting step responsive to the satisfaction of the loop stop criteria.

19. A computer processing system for clustering data elements to extract specific patterns from the data, the computer processing system comprising;
   a memory device including program code stored thereon;
   a hardware processor, operatively coupled to the memory device, and configured to run the program code stored on the memory device to
     specify, some of the data elements with a uniform distribution as a mini-batch;
     perform a single-pass cluster initialization by selecting a respective one of the data elements from the mini-batch as a respective initial cluster center to obtain a plurality of cluster centers for a plurality of clusters;
     assign each of the data elements in the mini-batch to a closest one of the plurality of clusters by calculating a distance between each of the data elements in the mini-batch and each of the plurality of clusters;
     assign k-minimum new centers by calculating an averaged distance to each of the data elements in a same one of the plurality of clusters;
     repeat the specifying step and the assigning steps responsive to a dissatisfaction of loop stop criteria which is based on distances between the plurality of centers and the K-minimum new centers being greater than or equal to a threshold;
     output a cluster id sequence responsive to a satisfaction of the loop stop criteria based on the distances being less than the threshold; and
     control a dispenser to automatically dispense an injection into a user to alter glucose levels of the user within expected limits responsive to sequence pattern mining results, obtained from a plot of the plurality of clusters, indicating abnormal glucose levels.

20. The computer-implemented method of claim 1, wherein said steps other than the automatically dispensing step are performed as a cloud service.

* * * * *